(12) United States Patent
Chalekian

(10) Patent No.: US 10,278,728 B2
(45) Date of Patent: May 7, 2019

(54) TRANSAPICAL MINI-INTRODUCER HEMOSTASIS VALVE AND PUNCH

(75) Inventor: Aaron J. Chalekian, Minneapolis, MN (US)

(73) Assignee: St. Jude Medical, LLC, Abbott Park, IL (US)

( * ) Notice: Subject to any disclaimer, the term of this patent is extended or adjusted under 35 U.S.C. 154(b) by 0 days.

(21) Appl. No.: 13/146,789

(22) PCT Filed: Jan. 29, 2010

(86) PCT No.: PCT/US2010/000249
§ 371 (c)(1),
(2), (4) Date: Jul. 28, 2011

(87) PCT Pub. No.: WO2010/087975
PCT Pub. Date: Aug. 5, 2010

(65) Prior Publication Data
US 2011/0282287 A1    Nov. 17, 2011

Related U.S. Application Data

(60) Provisional application No. 61/206,441, filed on Jan. 30, 2009.

(51) Int. Cl.
*A61B 17/34* (2006.01)
*A61B 17/3205* (2006.01)
*A61B 17/00* (2006.01)

(52) U.S. Cl.
CPC .... *A61B 17/3421* (2013.01); *A61B 17/32053* (2013.01); *A61B 17/3498* (2013.01);
(Continued)

(58) Field of Classification Search
CPC ............ A61B 17/3421; A61B 17/3461; A61B 17/3498; A61B 2017/00247;
(Continued)

(56) References Cited

U.S. PATENT DOCUMENTS 3,556,103 A * 1/1971 Calhoun ........... A61M 16/0472
128/200.26
4,177,814 A * 12/1979 Knepshield ............ A61B 10/04
604/167.04
(Continued)

FOREIGN PATENT DOCUMENTS

EP       1671596 A1     6/2006
WO       9631165 A1     10/1996
(Continued)

OTHER PUBLICATIONS

International Search Report and Written Opinion, PCT/US2010/000249, dated Jun. 1, 2010.
(Continued)

*Primary Examiner* — Nathan R Price
*Assistant Examiner* — Justin L Zamory
(74) *Attorney, Agent, or Firm* — Lerner, David, Littenberg, Krumholz & Mentlik, LLP

(57) ABSTRACT

An introducer for providing access to the interior of the heart generally includes a valve, a shaft, and a piercing element. The valve has a substantially closed state in the absence of an instrument inside the valve and an open state in the presence of the instrument inside the valve. The shaft has first and second ends. The piercing element is located at the first end of the shaft. The shaft is removably positioned inside the valve in an assembled condition. The valve is dimensioned to receive the instrument therein upon removal of the shaft from the valve.

15 Claims, 3 Drawing Sheets

(52) U.S. Cl.
CPC . *A61B 17/3462* (2013.01); *A61B 2017/00243* (2013.01); *A61B 2017/00247* (2013.01); *A61B 2017/346* (2013.01); *A61B 2017/3425* (2013.01); *A61B 2017/3488* (2013.01)

(58) Field of Classification Search
CPC ...... A61B 2017/3425; A61B 2017/346; A61B 2017/3488; A61M 2025/0233
See application file for complete search history.

(56) References Cited

U.S. PATENT DOCUMENTS

| | | | | |
|---|---|---|---|---|
| 4,291,690 | A | * | 9/1981 | Jessen ............... A61M 16/0472 128/200.26 |
| 4,601,710 | A | * | 7/1986 | Moll ................. A61B 17/3496 30/152 |
| 4,900,303 | A | | 2/1990 | Lemelson |
| 5,224,954 | A | * | 7/1993 | Watts ................ A61B 17/0218 606/205 |
| 5,290,249 | A | * | 3/1994 | Foster .................. A61B 17/34 604/174 |
| 5,330,437 | A | | 7/1994 | Durman |
| 5,395,342 | A | * | 3/1995 | Yoon ................. A61B 17/3421 604/167.03 |
| 5,603,702 | A | * | 2/1997 | Smith et al. .................. 604/256 |
| 5,649,959 | A | | 7/1997 | Hannam et al. |
| 5,653,730 | A | | 8/1997 | Hammerslag |
| 5,810,884 | A | | 9/1998 | Kim |
| 5,882,340 | A | * | 3/1999 | Yoon ........................ 604/164.12 |
| 6,113,641 | A | | 9/2000 | Leroy et al. |
| 6,174,322 | B1 | | 1/2001 | Schneidt |
| 6,475,177 | B1 | | 11/2002 | Suzuki |
| 7,008,439 | B1 | | 3/2006 | Janzen et al. |
| 7,771,454 | B2 | | 8/2010 | Michlitsch |
| 7,862,500 | B2 | | 1/2011 | Khairkhahan et al. |
| 8,182,530 | B2 | | 5/2012 | Huber |
| 8,257,389 | B2 | | 9/2012 | Chanduszko et al. |
| 8,454,708 | B2 | | 6/2013 | Kutsko et al. |
| 8,529,430 | B2 | | 9/2013 | Nikolic et al. |
| 8,870,914 | B2 | | 10/2014 | Hoffman et al. |
| 2002/0072767 | A1 | | 6/2002 | Zhu |
| 2002/0165581 | A1 | | 11/2002 | Brucker |
| 2002/0183787 | A1 | | 12/2002 | Wahr et al. |
| 2005/0004158 | A1 | | 1/2005 | Iyer et al. |
| 2005/0043759 | A1 | | 2/2005 | Chanduszko |
| 2006/0074484 | A1 | | 4/2006 | Huber |
| 2006/0167468 | A1 | * | 7/2006 | Gabbay ........................ 606/108 |
| 2007/0032823 | A1 | | 2/2007 | Tegg |
| 2007/0083229 | A1 | | 4/2007 | Deutsch |
| 2007/0123816 | A1 | | 5/2007 | Zhu et al. |
| 2007/0186934 | A1 | * | 8/2007 | DeLuca ............ A61M 16/0472 128/207.29 |
| 2007/0198060 | A1 | | 8/2007 | Devellian et al. |
| 2008/0004657 | A1 | | 1/2008 | Obermiller et al. |
| 2008/0114395 | A1 | | 5/2008 | Mathisen et al. |
| 2008/0215087 | A1 | | 9/2008 | Pavcnik et al. |
| 2008/0249474 | A1 | * | 10/2008 | Baker ............... A61B 17/3423 604/167.02 |
| 2008/0255650 | A1 | | 10/2008 | Kelley |
| 2008/0312684 | A1 | | 12/2008 | Drasler et al. |
| 2009/0062844 | A1 | | 3/2009 | Tekulve et al. |
| 2009/0069843 | A1 | | 3/2009 | Agnew |
| 2009/0088793 | A1 | | 4/2009 | Bagaoisan et al. |
| 2009/0171388 | A1 | | 7/2009 | Dave et al. |
| 2009/0177225 | A1 | | 7/2009 | Nunez et al. |
| 2009/0216265 | A1 | | 8/2009 | DeVries et al. |
| 2009/0216267 | A1 | | 8/2009 | Willard et al. |
| 2009/0227938 | A1 | | 9/2009 | Fasching et al. |
| 2009/0254110 | A1 | | 10/2009 | Bagaoisan et al. |
| 2013/0006297 | A1 | | 1/2013 | Drasler |

FOREIGN PATENT DOCUMENTS

| | | |
|---|---|---|
| WO | 97/17026 A1 | 5/1997 |
| WO | 9953852 | 10/1999 |
| WO | 03049619 A2 | 6/2003 |

OTHER PUBLICATIONS

Extended European Search Report for Application No. 17155634.3 dated May 17, 2017.

\* cited by examiner

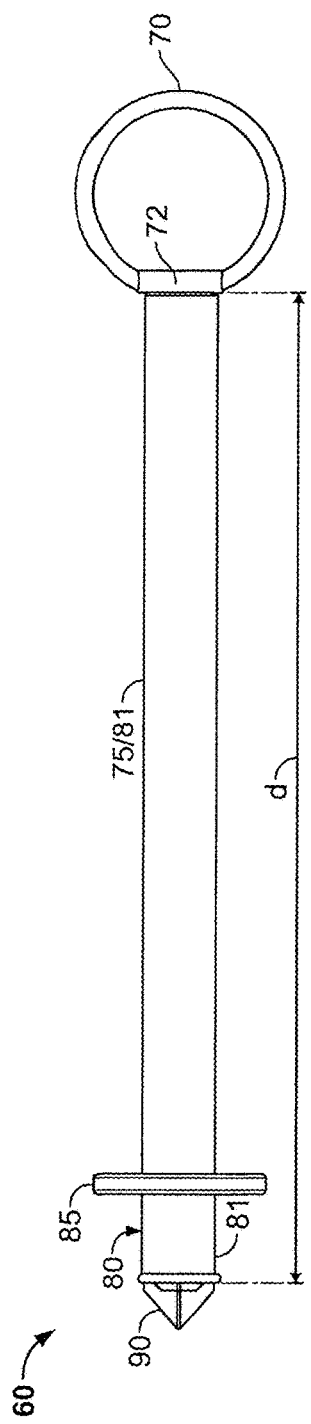
FIG. 5
FIG. 6

TRANSAPICAL MINI-INTRODUCER HEMOSTASIS VALVE AND PUNCH

CROSS-REFERENCE TO RELATED APPLICATIONS

This application is a national phase entry under 35 U.S.C. § 371 of International Application No. PCT/US2010/000249, filed Jan. 29, 2010, published in English, claims the benefit of the filing date of U.S. Provisional Patent Application No. 61/206,441, filed on Jan. 30, 2009, the entire disclosures of which are hereby incorporated herein by reference.

BACKGROUND OF THE INVENTION

During a cardiac valve repair or replacement procedure, access to the interior of the heart may be necessary. To access the interior of the heart, physicians often conduct a median sternotomy. In a median sternotomy, the physician makes an incision along the center of the chest to divide the patient's sternum, thereby creating an access to the heart. Sternotomies result in long recovery times and involve a high risk of complications (e.g., infections) due to the lengthy surgery required for these unstable patients.

Rather than performing the more invasive median sternotomy, a less invasive thoracotomy introducer device may be used to access the interior of the heart and to provide a conduit through which other devices may be passed during the procedure. Such miniaturized introducer aids the physician in inserting the necessary repair or replacement materials into the heart while also limiting the level of physical invasiveness and the amount of blood loss. Some less invasive introducers have been developed over the years. Improvements to these introducers are nonetheless still possible and desirable.

BRIEF SUMMARY OF TEE INVENTION

The present disclosure relates to introducers for providing access to the heart. An embodiment of the presently disclosed introducer generally includes a valve, a shaft, and a piercing element. The valve has a substantially closed state in the absence of an instrument inside the valve and an open state in the presence of the instrument inside the valve. The shaft has first and second ends. The piercing element is located at the first end of the shaft. The shaft is removably positioned inside the valve in an assembled condition. The valve is dimensioned to receive the instrument therein upon removal of the shaft from the valve.

In another embodiment, an introducer includes a valve having flaps movable between a substantially closed position in the absence of an instrument inside the valve and an open position in the presence of the instrument inside the valve, a shaft having a first end and a second end, and a punch at the first end of the shaft. The shaft is at least partially and removably positioned inside the valve in an assembled condition.

The present disclosure also relates to methods for accessing the interior of the heart. In one embodiment, the method includes providing an introducer including a valve having a proximal end and a distal end and a punch disposed through the valve; advancing the introducer toward the heart to pierce a myocardium of the heart with the punch of the punch; further advancing the introducer toward the heart punch until the valve is positioned at the myocardium; and removing the punch from the valve while leaving the valve positioned in the myocardium.

BRIEF DESCRIPTION OF THE DRAWINGS

A more complete appreciation of the subject matter of the present disclosure and the various advantages thereof can be realized by reference to the following detailed description in which reference is made to the accompanying drawings in which:

FIG. 5 is a side view of a transapical introducer according to another embodiment of the present disclosure; and FIG. 6 is an isometric view of the transapical introducer of FIG. 5.

DETAILED DESCRIPTION

Figure 1:
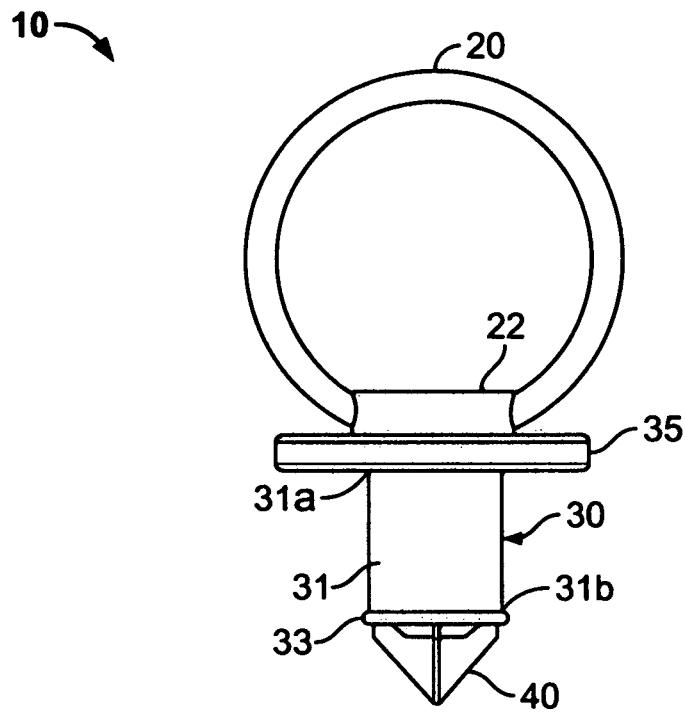
FIG. 1 is a side view of a transapical mini-introducer according to an embodiment of the present disclosure.

FIGS. 1-4 show a transapical mini-introducer 10 according to an embodiment of the present disclosure. Mini-introducer 10 includes a feature for puncturing tissue (e.g., myocardium) and another feature for providing access to the interior of the heart. These features are coupled together. Consequently, a separate introducer sheath and a delivery device are not needed. The use of mini-introducer 10 minimizes bleeding and drops in blood pressure experienced when switching between puncture and introduction of a delivery device or an introducer sheath.

Mini-introducer 10 generally includes a ring 20, a hemostasis valve 30, and a punch or piercing element 40 configured to pierce cardiac tissue such as the myocardium. In some embodiments, punch 40 and hemostasis valve 30 can be integrated into a standard introducer. Punch 40 is coupled to ring 20. Ring 20 is releasably connected to hemostasis valve 30. Consequently, punch 40 and ring 20 can be separated from hemostasis valve 30. Mini-introducer 10 may be made of any suitable material capable of withstanding the force imposed when punch 40 punctures the myocardium at the apex and when ring 20 is pulled or grasped to separate punch 40 from hemostasis valve 30.

Figure 3:
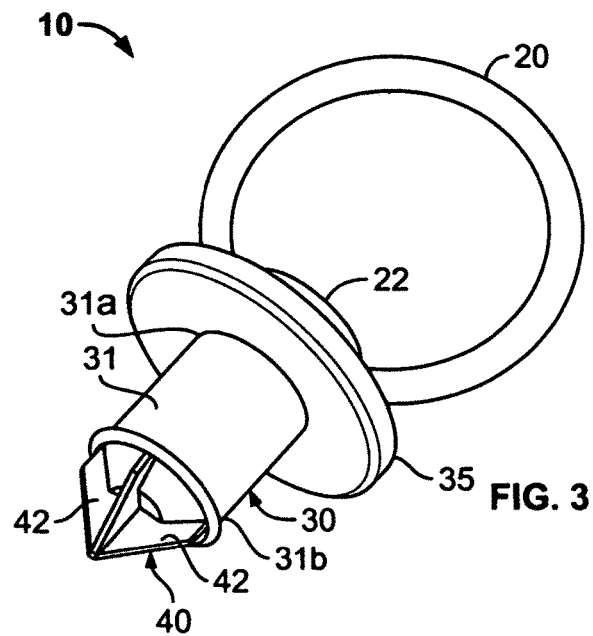
FIG. 3 is an isometric front view of the transapical mini-introducer of FIG. 1.
Figure 4:
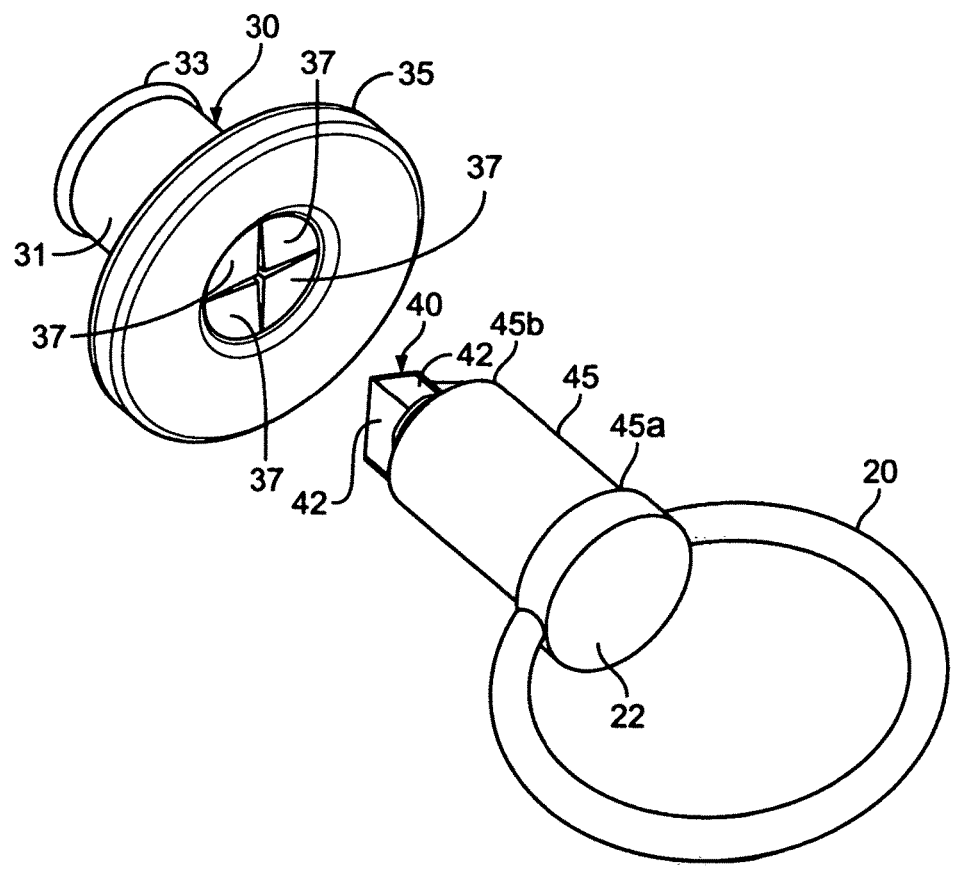
FIG. 4 is an isometric exploded view of the transapical introducer of FIG. 1.

With reference to FIGS. 3 and 4, ring 20 includes a base 22 and may be wholly or partly made of a material capable of withstanding the force imposed when a user (e.g., physician) or another instrument pulls, twists, or otherwise manipulates ring 20 to remove punch 40 from the myocardium. The diameter of ring 20 may vary depending on whether ring 20 is intended to be grasped by the user or by a grasping instrument. Ring 20 is connected to punch 40 through shaft 45. Shaft 45 includes a first end 45a attached to base 22 of ring 20 and a second end 45b connected to punch 40.

In some embodiments, punch 40 includes four blades oriented substantially orthogonal to one another. Punch 40, however, may have more or fewer blades with any other shape or configuration suitable for puncturing the myocardium at the apex of the heart. In other embodiments, punch 40 may have a tapered or pointed shape. Irrespective of its shape, punch 40 is made wholly or partially of any material capable of puncturing the myocardium at the apex to access the interior of the heart without causing undue tissue damage.

Hemostasis valve 30 includes a tube or hollow member 31, which defines a bore or cavity (not shown). Hollow member 31 has a first end 31a and a second end 31b. First end 31a of hollow member 31 includes a shoulder 35 for abutting the apex of the heart, whereas second end 31b of hollow member includes an annular rib 33 for assisting in securing hemostasis valve 30 to the heart. Hemostasis valve 30 may (additionally or alternatively) include multiple ribs 33 spaced along its axial length.

Hemostasis valve 30 further includes flexible flaps (or any other suitable seal) positioned within the bore of hollow member 31 and adjacent to first end 31a. Flaps 37 may be wholly or partly made of silicon or any other resilient material suitable for permitting the passage of devices through hemostasis valve 30 while also preventing, or at least minimizing, blood leakage from the heart and limiting any drop in blood pressure. In the embodiment depicted in FIG. 4, hemostasis valve 30 includes four flaps 37 defining a cross-shaped slit, but hemostasis valve 30 may include more or fewer flaps. Regardless of the shape or number of flaps 37, the flaps are adapted to move between a substantially closed position (FIG. 4) in the absence of an instrument inside hemostasis valve 30 and an open position in the presence of an instrument within hemostasis valve 30. In the substantially closed position, flaps 37 prevent, or at least inhibit, blood from exiting the heart through hemostasis valve 30. In the open position, flaps 37 allow passage of one or more instruments or devices through the bore of hollow member 31. Hemostasis valve 30 may incorporate a duckbill seal instead of or in addition to flaps 37.

Figure 2:
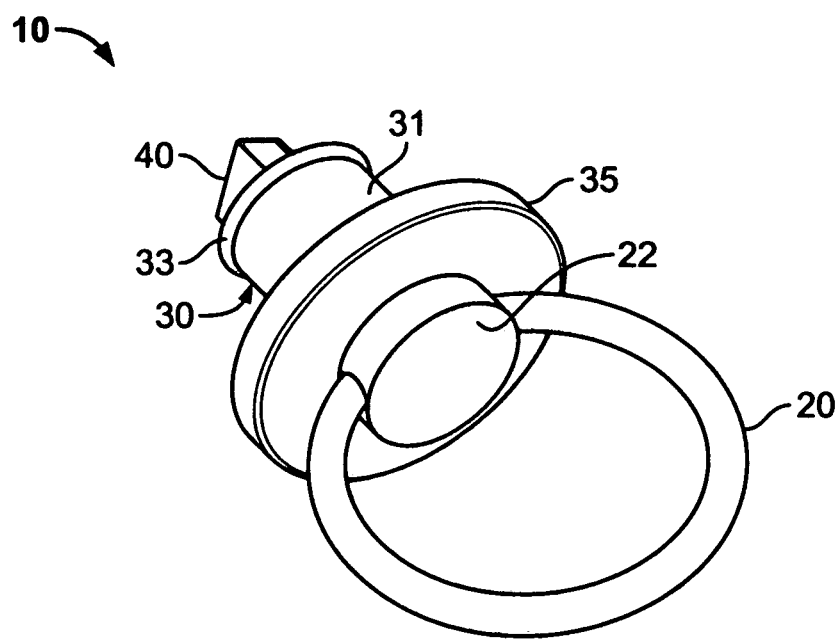
FIG. 2 is an isometric rear view of the transapical mini-introducer of FIG. 1.

The bore of hollow member 31 is dimensioned to receive shaft 45 and extends from first end 31a to the second end 31b of hollow member 31. To assemble mini-introducer 10, hemostasis valve 30 is positioned over punch 40 and shaft 45 until shoulder 35 abuts base 22 of ring 20. At this point, base 22 of ring 20 substantially or completely covers an opening leading to the bore of hollow member 31, as shown in FIG. 2. Once mini-introducer 10 has been assembled, shaft 45 is at least partially positioned inside hollow member 31 and punch 40 extends beyond second end 31b of hollow member 31. When shaft 45 is positioned inside hemostasis valve 30, hollow member 31 (completely or substantially) encloses shaft 45.

In some embodiments, mini-introducer 10 may include a detent release mechanism, such as a ball detent mechanism, to provide some resistance to the separation of ring 20 and punch 40 from hemostasis valve 30. The resistance produced by the detent release mechanism may be overcome by deliberate action to remove punch 40 from hemostasis valve 30.

In certain embodiments, the length of hemostasis valve 30 measured from first end 31a to second end 31b is about 0.5 inches. This length may ensure that the second end 31b of hemostasis valve 30 has accessed the interior of the heart without injuring the papillary muscles or the chordae. The length of the hemostasis valve 30 may be substantially similar to the length of shaft 45.

In any surgical procedure requiring access to the interior of the heart, a user (e.g., physician or other health care professional) may employ mini-introducer 10 for establishing a conduit for passage of other devices or instruments into the heart while also minimizing blood loss and drops in blood pressure due to puncturing the apex. Mini-introducer 10 could be provided in a pre-assembled condition or may require assembly by the user. To assemble mini-introducer 10, the user slides hemostasis valve 30 over punch 40 and shaft 45 until shoulder 35 abuts base 22 of ring 20. Once assembled, shaft 45 is at least partially positioned inside hollow member 31 and punch 40 extends beyond second end 31b of hollow member 31.

The user may gain access to the heart by performing a thoracotomy, spreading the incision, and moving the tissue or organs (e.g., the pericardium and the lungs) obstructing the user's view of the heart. The thoracotomy may be performed between the fifth and sixth intercostal spaces with, for example, a two to three inch incision. A purse string suture may be sewn at the apex of the heart using any suitable approach. Punch 40 may be aligned such that its tip is placed at the center of the purse string suture. Then, the user may grab ring 20 (directly or via a grasping implement or device) and advance mini-introducer 10 toward the patient's heart to puncture the myocardium at the apex with punch 40, thereby creating an access opening to the interior of the patient's heart. The puncture is preferably created at the apex, where the myocardium is the thinnest. Mini-introducer 10 is pushed toward the heart until shoulder 35 abuts the apex. The purse string suture may then be cinched, or drawn, about mini-introducer 10.

While holding shoulder 35 against the apex, the user may separate ring 20 and punch 40 from hemostasis valve to leave the valve transapically positioned in the myocardium. To remove ring 20 and punch 40 from hemostasis valve 30, the user applies a pulling or twisting force to ring 20. This force may be applied directly by the user or through a grasping implement or instrument. In any case, ring 20 is pulled, twisted, or otherwise released from hemostasis valve 30 until ring 20 and punch 40 are removed from the patient, leaving hemostasis valve 30 behind in the myocardium. At this point, hemostasis valve 30 provides a conduit into the homeostatic environment (e.g., cardiopulmonary system) while also limiting both the amount of blood lost through the punctured myocardium and the drop in blood pressure that may occur as a result of accessing the interior of the heart. One or more instruments or devices, such as valvuloplasty balloons or collapsible prosthetic valve delivery systems, can be inserted into the patient's heart through the conduit created by hemostasis valve 30. When the user introduces an instrument through hemostasis valve 30, flaps 37 bend to permit passage of the instrument. Upon removal of the instrument, flaps 37 resiliently return to their original position, as shown in FIG. 4. In the original position, flaps come together in the interior of hemostasis valve 30, thereby preventing, or at least inhibiting, blood from flowing out of the heart via hemostasis valve 30.

Another embodiment of the present invention may be configured so that the base 22 does not abut shoulder 35 in the assembled condition. A transapical introducer 60 in accordance with this embodiment is illustrated in FIGS. 5 and 6. Transapical introducer 60 is similar to, and that may include some or all of the features of, transapical mini-introducer 10. Ring 70, hemostasis valve 80, shoulder 85, and punch 90 may include some or all the features of ring 20, hemostasis valve 30, and punch 40, respectively. For example, hemostasis valve 80 includes a tube or hollow member 81 and a shoulder 85. Transapical introducer 60, however, includes an elongated shaft 75 instead of the shorter shaft 45 of transapical mini-introducer 10. Elongated shaft 75 connects ring 70 to punch 90. While shaft 45 of transapical mini-introducer 10 has a length that permits base 22 of ring 20 to abut shoulder 35 when punch 40 projects from the second end 31b of valve 30 (e.g., resulting in a distance of about 0.5 inches from base 22 to punch 40 in one embodiment), shaft 75 of transapical introducer 60 may have any length suitable to create a greater distance d (e.g., about six inches) between base 72 of ring 70 and punch 90. In some embodiments, hollow member 81 extends beyond shoulder 85 toward ring 70. In those embodiments, a portion of hemostasis valve 80 may be positioned around elongated shaft 75 between shoulder 85 and ring 70.

The length of shaft 75 between shoulder 85 and punch 90 may be about the same as the length of shaft 45 (e.g., 0.5 inches), but shoulder 85 may be located at a greater distance (e.g., about 5.5 inches) from base 72 of ring 70 in comparison to the distance between shoulder 35 and ring 20 of mini-introducer 10. A larger distance between ring 70 and shoulder 85 permits ring 70 to reside outside of the patient's body rather than being introduced into and later extracted from the patient's body. The method of using transapical introducer 60 is substantially similar to the method of using transapical mini-introducer 10 described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, shafts 45 and 75 may have other lengths than those described and rings 20 and 70 may have other configurations.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. An introducer for providing access to the heart, comprising:
    a tubular body extending continuously from an entrance end to an exit end;
    a valve assembled in the body, the valve having a substantially closed state in the absence of an instrument inside the valve and an open state in the presence of the instrument inside the valve;
    an annular rib at the exit end of the body and configured to secure the body to the heart, the annular rib having a circumference of the same size in both the closed state of the valve and in the open state of the valve;
    a shoulder positioned between the exit end of the body and the entrance end of the body, the shoulder being at a first spaced distance from the exit end of the body and at a second spaced distance from the entrance end of the body, the second spaced distance being greater than the first spaced distance;
    a shaft having a first end and a second end; and
    a piercing element at the first end of the shaft, the shaft being positioned inside the valve in an assembled condition so that the shaft and the valve may be inserted together through tissue of the heart, in the assembled condition the piercing element being exposed for use beyond the exit end of the body and the second end of the shaft being at the entrance end of the body so that the distance between the second end of the shaft and the shoulder is greater than the first spaced distance, and the valve being dimensioned to receive the instrument therein upon removal of the shaft from the valve.

2. The introducer according to claim 1, further comprising a grasping member connected to the second end of the shaft.

3. The introducer according to claim 1, wherein the shoulder is at the entrance end of the body.

4. The introducer according to claim 1, wherein the piercing element includes a plurality of blades.

5. The introducer according to claim 1, wherein the valve includes a plurality of flaps resiliently movable between a substantially closed position in the absence of the instrument inside the valve and an open position in the presence of the instrument inside the valve.

6. The introducer according to claim 5, wherein the flaps collectively define a cross-shaped slit in the substantially closed position.

7. The introducer according to claim 1, wherein the body has a length, and the shaft has a length which is substantially the length of the body.

8. The introducer according to claim 1, wherein the body has a length, and the shaft has a length which is greater than the length of the body.

9. An introducer for providing access into a heart, comprising:
    a tubular body having an entrance end, an exit end, and an annular rib at the exit end, the annular rib being configured to secure the body to the heart;
    a valve assembled in the body, the valve including flaps movable between a substantially closed position in the absence of an instrument inside the valve and an open position in the presence of the instrument inside the valve, the flaps in the closed position collectively defining substantially a plane, the annular rib having a circumference of the same size in both the absence of the instrument inside the valve and in the presence of the instrument inside the valve;
    a shoulder at a spaced distance from the exit end of the body and positioned between the entrance end of the body and the exit end of the body;
    a shaft having a first end and a second end; and
    a punch at the first end of the shaft;
    the shaft being positioned inside the valve in an assembled condition so that the shaft and the valve may be inserted together through tissue of the heart, in the assembled condition the punch being exposed for use beyond the exit end of the body and the distance between the second end of the shaft and the shoulder being greater than the spaced distance.

10. The introducer according to claim 9, further comprising a ring connected to the second end of the shaft.

11. The introducer according to claim 9, wherein the punch includes a plurality of blades.

12. The introducer according to claim 9, wherein the flaps collectively define a cross-shaped slit in the substantially closed position.

13. The introducer according to claim 9, wherein the body has a length, and the shaft has a length which is substantially the length of the body.

14. The introducer according to claim 9, wherein the body has a length, and the shaft has a length which is greater than the length of the body.

15. The introducer according to claim 1, further comprising a detent release mechanism for holding the shaft in assembled relationship to the body.

* * * * *